United States Patent [19]

Peterson et al.

[11] 4,441,504
[45] Apr. 10, 1984

[54] ELECTRONIC CUFF TO MONITOR BLOOD PRESSURE IN POLYGRAPH INSTRUMENTS

[75] Inventors: Donald A. Peterson, Berwyn; Henry K. Skrzypczak, Westchester, both of Ill.

[73] Assignee: Stoelting Company, Chicago, Ill.

[21] Appl. No.: 376,675

[22] Filed: May 10, 1982

[51] Int. Cl.³ .............................................. A61B 5/02
[52] U.S. Cl. .................................... 128/686; 128/677
[58] Field of Search ............... 128/686, 677, 690, 327, 128/900

[56] References Cited

U.S. PATENT DOCUMENTS 2,714,379  8/1955  Raines .................................. 128/900
2,753,863  7/1956  Bailey ............................. 128/686 X
3,095,873  7/1963  Edmunds, Jr. ....................... 128/686
4,206,765  6/1980  Huber ............................. 128/686 X

FOREIGN PATENT DOCUMENTS 894071  12/1944  France ................................. 128/686

OTHER PUBLICATIONS

"Silicon Transducer Strapped to Wrist Reads Blood Pressure"; *Electronics Review*; vol. 50, No. 9, 1974–1977, pp. 29–30.

Primary Examiner—Kyle L. Howell
Assistant Examiner—Angela D. Sykes
Attorney, Agent, or Firm—William A. Snow

[57] ABSTRACT

This invention relates to an electronic cuff to monitor blood pressure which is non-invasive and non-pneumatic for high fidelity recording for use in polygraph recorders.

8 Claims, 7 Drawing Figures

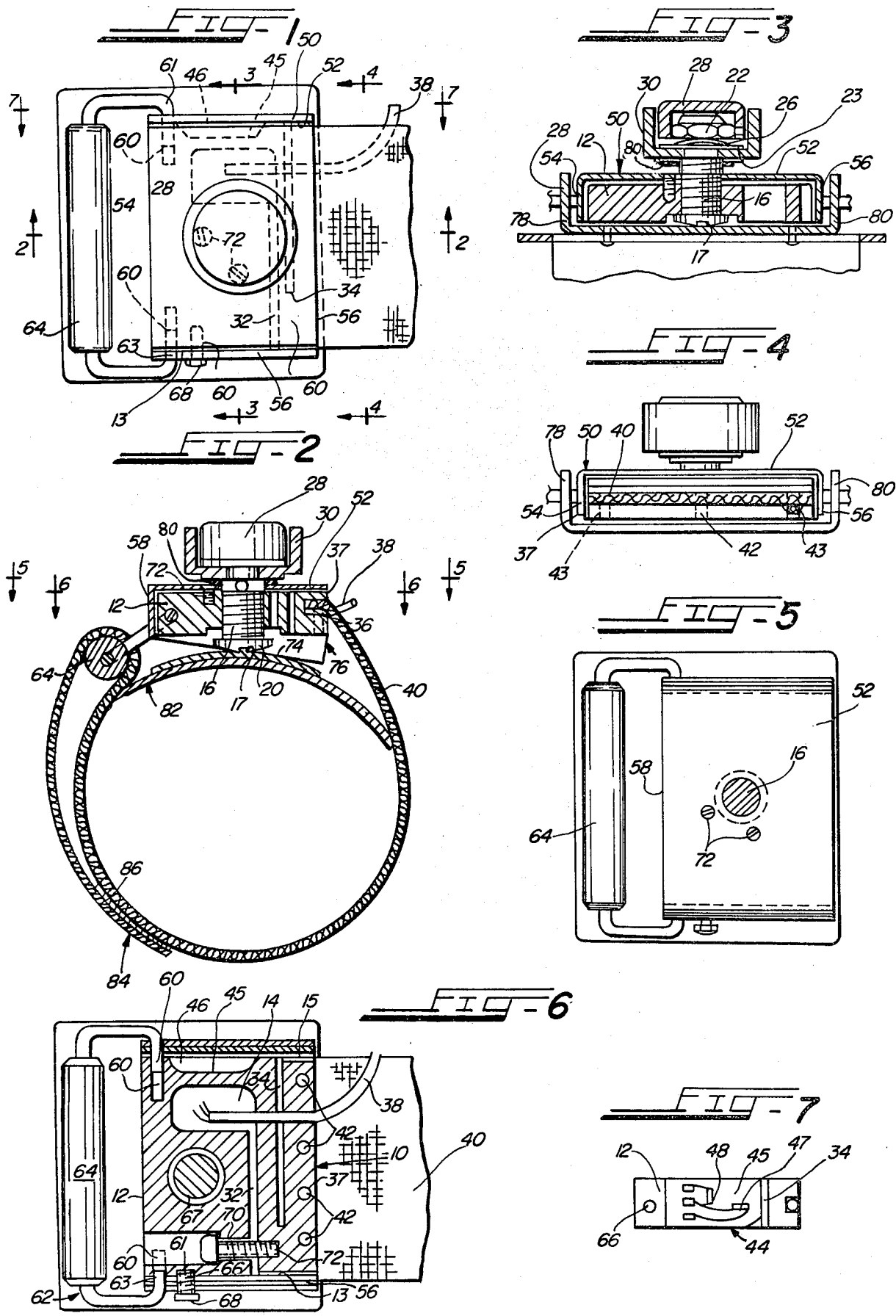

ELECTRONIC CUFF TO MONITOR BLOOD PRESSURE IN POLYGRAPH INSTRUMENTS

BACKGROUND OF THE INVENTION

Most cuffs used by polygraph examiners are pneumatic and are strapped around the arm of the subject to be interrogated and inflated usually higher than necessary to substantially occlude the artery to obtain a reading on a graph of a polygraph instrument and remain on the arm for long periods of time and therefore hinder or occlude the flow of blood in the arm; thus examination must be shortened. The testing procedure is tiring, tedious and possibly traumatic.

It was to overcome this problem in the polygraph field that the present invention was conceived.

SUMMARY OF THE INVENTION

A non-invasive, non-pneumatic cuff having a pair of strain gauges mounted on a metal load cell and the cell having a hinged saddle thereon to which a curved plate is anchored, and a tensioning screw on the load cell contacting the saddle and plate, a clutch associated with said screw to automatically set the maximum recording tension on the arm of a subject after a Velcro strap has been appropriately placed on the arm of the subject. The present invention is a linear, solid-state cardio sensor and the silicon strain gauges are connected to a recording channel of a polygraph instrument through a cable and connector.

BRIEF DESCRIPTION OF THE DRAWINGS

FIG. 1 is a top view of the electronic cuff with parts shown in dash outline;

FIG. 2 is a cross-sectional view taken on the lines 2—2 of FIG. 1 and illustrating the Velcro strap as it would be wrapped around the arm;

FIG. 3 is a cross-sectional view taken on the lines 3—3 of FIG. 1;

FIG. 4 is a partial cross-sectional view taken on the lines 4—4 of FIG. 1;

FIG. 5 is a partial cross-sectional view taken on the lines 5—5 of FIG. 2 with parts omitted for clarity;

FIG. 6 is a partial cross-sectional view taken on the lines 6—6 of FIG. 2; and

FIG. 7 is a partial cross-sectional view taken on the lines 7—7 of FIG. 1.

DETAILED DESCRIPTION OF THE DRAWINGS

The present invention relates to an electronic, linear, solid-state cardio sensor cuff used for polygraph recordings and for obtaining the highest fidelity recording on a graph having larger base line changes and a more distinct graph.

The drawings illustrate a load cell 10 comprising an aluminum base 12 with a cutout portion 14, said base being drilled and tapped medially and vertially to support a screw 16. A circular Nylon washer is secured to the free end of the screw 16 by screws 17. A clutch nut 22 is used to adjust the clutch for desired torque and it is secured by screw 16. The nut 22 is covered by a snap cover 28. A rotatable clutch knob 30 is held by friction force between clutch plates.

The cutout portion 14 of the aluminum base 12 is provided with a longitudinal cleft 32 extending from the cutout 14 to the opposite end wall of the base 12. The cleft 34 extends from the opposite end wall 15 about three-quarters of the way across the base 12 and spaced from cleft 32 and the side wall 37. An edgewise channel 36 is placed in the wall 37 and extends from end-to-end to support one end of the cable 37 and one end of a Velcro strap 40 by screws 42 anchored in tapped apertures 43 in the bottom wall of the aluminum base. The cable 38 contains wires connected to a pair of silicon strain gauges generally indicated at 44 (see FIG. 7) mounted on the outer side of the wall 45 set back from wall 15 and in the recess 46. The opposite end of the cable is provided with a connector which is connected to a polygraph apparatus channel (not shown but well understood in the art).

The strain gauges 44 consist of a compensation gauge 48 and a compression gauge 47, all as shown in FIG. 7.

A cover 50 covers the base 12 and comprises a top wall 52, side walls 54, 56 and one end wall 58 and has a medial aperture in the top wall, through which the screw 16 extends. Also, the side walls 54, 56 are provided with opposed apertures and the end walls 13, 15 are provided with opposed seats 60 aligned with the aforesaid apertures in which the ends 61, 63 of the saddle 62 rotatively seat. The saddle carries a roller 64 around which the strap 40 is positioned. (See FIG. 2.)

A second aperture is provided in the side wall 56 aligned with a threaded seat 66 to support a headed screw 68 and limit the pivoting of the cover 50. The top wall 52 is provided with spaced apertures under the knob 30 and aligned with drilled and tapped seats to receive screws 72 to support the cover. There is a clearance between cover 50 and base 12, as shown in FIGS. 1, 2, 4 and 6.

The screw 70 is the limit screw to prevent abusive damage to the load cell.

A saddle 76 comprises an arcuate plate 74 having side walls 78, 80 pivotally secured to the cover and base by the ends 61 and 63 of saddle 62, as shown in FIG. 3. A curved, thin plate 82 is riveted to the plate 74, as shown in FIG. 2, which plate is placed on the arm of the subject to be tested.

In operation, the polygraph examiner places the curved plate 82 on the upper arm or forearm of the subject to be interrogated and by inserting the end of the Velcro strap 40 through and around the roller 64, and very slightly tautening the same on the arm and then engaging the hook end 84 of the strap 40 to the loop 86 of the strap, fastens the strap in position. The knob 30 is turned clockwise so that the Nylon washer 20 exerts pressure on the saddle. Upon further turning of the knob, the slip clutch slips. The slip clutch is calibrated to slip at predetermined strap tension required for proper operation of the cuff. The strain gauge 47 on the wall 45 of the load cell 10 senses the micro strain forces created in the load cell by the blood pressure changes in the arm of the subject. The resulting electrical signal from the strain gauge passes through the wires in the cable 38 and is amplified by the recording instrument (not shown but well known in the art).

Thus the recording instrument produces graphs showing deviations created by the pressure changes in the arm of the subject. The unit is worn without discomfort to the subject and can be worn for long periods of time.

To automatically and repeatedly adjust strap tension in the cuff, the mechanism consisting of two plates connected at one end by a pivot separated by a clutch screw driven by the slip clutch was designed. As the two pivoting plates separate, the cross-section of the arm decreases and the strap tension increases. To limit the tension, the slip clutch is adjusted to slip at the predetermined strap tension.

The slip clutch consists of a stainless steel screw 16, two stainless steel "D" clutch plates, one on each side of the plastic (Delrin) clutch knob 30, two spring bowed washers providing the clutch tension, tension adjusting, self retaining nut 22, snap nut cover 28, Teflon anti-lock washer 80 and dual purpose Nylon washer 20 attached with flat head screw to clutch screw 16. One function of the Nylon washer is to provide smooth contact between the screw 16 and the pivot plate. The other function is to retain the clutch screw within the housing when the clutch knob is turned in the opposite direction. The slots in the knob 30 and the holes in the snap cap are in aid in the determination of the tension in the arm cuff strap. When the slots and the holes move in unison, the tension in the cuff is inadequate and the knob needs to be turned until there is relative motion between the holes and the slots. If the initial pretensioning of the strap was correct, the clutch should slip before contact is made between the teflon washer and cover plate 50. If contact is made between the washer and the cover, turn clutch knob in the opposite direction, retighten the Velcro strap slightly and repeat the tensioning procedure.

Although but one specific embodiment of this invention is herein shown and described, it will be understood that details of the construction shown may be altered or omitted without departing from the spirit of the invention as defined by the following claims.

We claim:

1. A non-invasive, non-pneumatic cuff for use in polygraph testing comprising a load cell, strain gauges on said load cell adapted to be connected to a polygraph instrument by a cable, a curved plate pivotally connected to said load cell, a combination screw and clutch to properly pressurize the plate and load cell against the arm of a subject to be examined, an arm band being adapted to secure said plate and load cell to the arm of the subject, said arm band having two ends, said load cell being provided with an end channel, one end of said arm band being securely anchored in said end channel.

2. The device according to claim 1 wherein the load cell is aluminum with cutouts therein and spaced, oppositely-extending clefts said strain gauges are mounted in one of said cutouts of said load cell whereby any change in the blood pressure of the subject under examination will be picked up by said load cell through said strain guages and be imparted to the polygraph instrument.

3. The device according to claim 2 wherein said load cell is drilled and tapped to receive said screw, said screw, said screw having an end and being provided with a nylon washer on said end to bear against said curved plate, and a knob to manipulate said screw.

4. The device according to claim 3 wherein a saddle is secured to said curved plate, said saddle having side walls pivotally secured to said load cell.

5. The device according to claim 4 wherein a second saddle is pivotally secured to said load cell and a cylindrical roller is rotatively secured thereon.

6. The device according to claim 5 wherein said arm band is a Velcro strap, and is passed around said roller to apply the load cell to the arm of the subject.

7. The device according to claim 4 wherein means are provided in the load cell to limit rotation of the saddle.

8. The device according to claim 2 wherein the strain gauges comprise a compensation gauge and a compression gauge.

* * * * *